(12) United States Patent
Broderick et al.

(10) Patent No.: US 9,518,023 B2
(45) Date of Patent: Dec. 13, 2016

(54) SYNTHESIS OF N-DERIVATIZED LACTAM BASED IONIC LIQUID

(71) Applicant: UOP LLC, Des Plaines, IL (US)

(72) Inventors: Erin M. Broderick, Arlington Heights, IL (US); Alakananda Bhattacharyya, Glen Ellyn, IL (US); Alan B. Levy, Randolph, NJ (US); Lihao Tang, Bridgewater, NJ (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/271,319

(22) Filed: May 6, 2014

(65) Prior Publication Data

US 2015/0322017 A1    Nov. 12, 2015

(51) Int. Cl.
*C07D 223/04* (2006.01)
*C07D 223/10* (2006.01)
*C07C 309/30* (2006.01)
*C07D 209/34* (2006.01)
*C07C 303/32* (2006.01)

(52) U.S. Cl.
CPC ............ *C07D 223/10* (2013.01); *C07C 303/32* (2013.01); *C07C 309/30* (2013.01); *C07D 209/34* (2013.01)

(58) Field of Classification Search
CPC .................................................. C07D 223/04
See application file for complete search history.

(56) References Cited

U.S. PATENT DOCUMENTS

| | | | |
|---|---|---|---|
| 7,220,869 | B2 | 5/2007 | Deng et al. |
| 7,285,698 | B2 | 10/2007 | Liu et al. |
| 2006/0135839 | A1 | 6/2006 | Elomari et al. |
| 2007/0021604 | A1 | 1/2007 | Deng et al. |
| 2007/0142676 | A1 | 6/2007 | Elomari et al. |
| 2007/0225538 | A1 | 9/2007 | Elomari |

FOREIGN PATENT DOCUMENTS

| | | |
|---|---|---|
| CN | 1943872 A | 4/2007 |
| CN | 1978431 A | 6/2007 |
| CN | 1978434 A | 6/2007 |
| CN | 101985435 A | 3/2011 |
| EP | 2520558 A1 | 11/2012 |

OTHER PUBLICATIONS

Yang et al. (Helvetica Chimica Acta (2010), 93(8), 1653-1660.*
Jiang et al. (Chinese Journal of Chemical Engineering (2013), 21(7), 766-769). Abstract.*
Marvel et al. (Journal of Organic Chemistry (1957), 22, 1065-1067).*
Nie et al. (Zhongguo Yiyao Gongye Zazhi (1993), 24(4), 147). Abstract.*
Zhou et al. (Youse Jinshu (2002), 54(3), 39-40, 44). Abstract.*
Yang et al., "Novel Ionic Liquid Crystals Based on N-Alkylcaprolactam as Cations," Chemistry Materials (2007), 19(10), 2544-2550.
Du et al., "Investigation of Physicochemical Properties of Lactam-Based Bronsted Acidic Ionic Liquids," Journal of Physical Chemistry B (2005), 109(41), 19542-19546.
Fabos et al., "ε-Caprolactamium Hydrogen Sulfate: An Ionic Liquid Used for Decades . . . " ChemSusChem (2008), 1(3), 189-192.
Guo et al., "Clean Beckmann rearrangement of cyclohexanone oxime in caprolactam-based Bronsted acidic ionic liquids", Green Chemistry (2006), vol. 8, 296-300.
Guo et al., "Absorption and Oxidation of H2S in Caprolactam Tetrabutyl Ammonium Bromide Ionic Liquid," Energy & Fuels (2011), vol. 25, 159-161.
Jiang et al., "Thermodynamic Properties of Caprolactam Ionic Liquids," Chinese Journal of Chemical Engineering (2013), 21(7), 766-769.

* cited by examiner

*Primary Examiner* — Bruck Kifle

(57) ABSTRACT

Lactamium based ionic liquids and methods of making them are described. The ionic liquids comprise at least one of: the reaction product of a lactam compound having a general formula

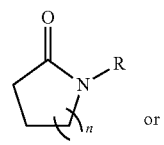

(IV)

or

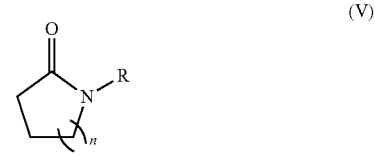

(V)

wherein the ring has at least one C═C double bond, or

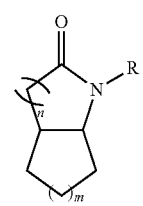

(VI)

and a Brønsted acid HX; or a Brønsted acid HX where X is a halide, and a metal halide.

1 Claim, No Drawings

SYNTHESIS OF N-DERIVATIZED LACTAM BASED IONIC LIQUID

BACKGROUND OF THE INVENTION

Ionic liquids are of interest to industry because of their wide range of applications, including use as solvents and catalysts. Ionic liquids are salts comprised of cations and anions which typically melt below about 100° C.

Ionic liquids are described in U.S. Pat. Nos. 4,764,440, 5,104,840, and 5,824,832, for example. The properties vary extensively for different ionic liquids, and the use of ionic liquids depends on the properties of a given ionic liquid. Depending on the organic cation of the ionic liquid and the anion, the ionic liquid can have very different properties.

However, the cost of ionic liquids has limited the widespread adoption of ionic liquids.

There is a need for lower cost ionic liquids and for methods of making them.

SUMMARY OF THE INVENTION

One aspect of the present invention is an ionic liquid having a lactam based cation. In one embodiment, the ionic liquid has a general formula of at least one of:

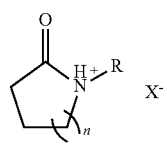
(I)

wherein R is an alkyl group having from 1 to 12 carbon atoms, an amine, an ether, or a silyl group, n is 1 to 8, and $X^-$ is an anion group of a Brønsted acid HX or a halometallate, with the proviso that when n is 3, and $X^-$ is p-toluenesulfonate, and R is the alkyl group, the alkyl group has from 1 to 5 carbon atoms;

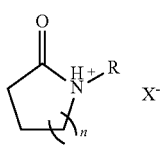
(II)

wherein the ring has at least one C=C double bond, R is an alkyl group having from 1 to 12 carbon atoms, an amine, an ether, or a silyl group, n is 1 to 8, and $X^-$ is an anion group of a Brønsted acid HX or a halometallate;

or

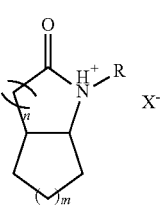
(III)

wherein R is an alkyl group having from 1 to 12 carbon atoms, an amine, an ether, or a silyl group, n is 1 to 8, m is 1 to 8, $X^-$ is an anion group of a Brønsted acid HX or a halometallate, and the rings can be saturated or unsaturated.

In one embodiment, ionic liquid comprises at least one of:

the reaction product of a lactam compound having a general formula

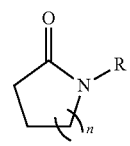
(IV)

wherein R is an alkyl group having from 1 to 12 carbon atoms, an amine, an ether, or a silyl group, n is 1 to 8, and a Brønsted acid HX; or a Brønsted acid HX, where X is a halide, and a metal halide;

with the proviso that when n is 3, and the reaction product is p-toluenesulfonate, and R is the alkyl group, the alkyl group has from 1 to 5 carbon atoms;

or the reaction product of a lactam compound having a general formula

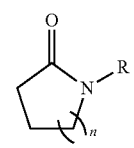
(V)

wherein the ring has at least one C=C double bond, R is an alkyl group having from 1 to 12 carbon atoms, an amine, an ether, or a silyl group, and n is 1 to 8, and a Brønsted acid HX; or a Brønsted acid HX, where X is a halide, and a metal halide;

or the reaction product of a lactam compound having a general formula

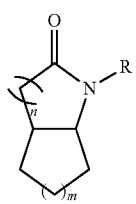
(VI)

wherein R is an alkyl group having from 1 to 12 carbon atoms, an amine, an ether, or a silyl group, n is 1 to 8, and m is 1 to 8, and the rings can be saturated or unsaturated;

and a Brønsted acid HX; or a Brønsted acid HX, where X is a halide, and a metal halide.

Another aspect of the invention is a method of making an ionic liquid having a lactam cation. In one embodiment, the method includes at least one of:

reacting a lactam compound having a general formula

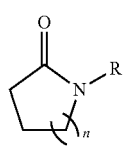
(IV)

wherein R is an alkyl group having from 1 to 12 carbon atoms, an amine, an ether, or a silyl group, n is 1 to 8;

with a Brønsted acid HX; or a Brønsted acid HX, where X is a halide, and a metal halide;

with the proviso that when n is 3, the reaction product is p-toluenesulfonate, and R is the alkyl group, the alkyl group has from 1 to 5 carbon atoms;

or reacting a lactam compound having a general formula

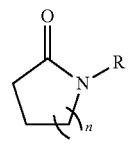
(V)

wherein the ring has at least one C═C double bond, R is an alkyl group having from 1 to 12 carbon atoms, an amine, an ether, or a silyl group, and n is 1 to 8, with a Brønsted acid HX; or a Brønsted acid HX where X is a halide, and a metal halide;

or reacting a lactam compound having a general formula

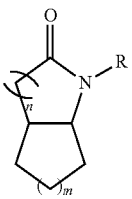
(VI)

wherein R is an alkyl group having from 1 to 12 carbon atoms, an amine, an ether, or a silyl group, n is 1 to 8, and m is 1 to 8, and the rings can be saturated or unsaturated;

with a Brønsted acid HX; or a Brønsted acid HX, where X is a halide, and a metal halide.

DETAILED DESCRIPTION OF THE INVENTION

The present invention provides cost effective ionic liquids capable of being produced on an industrial scale. The ionic liquids are N-derivatized lactamium based ionic liquids. Lactam compounds can be converted to the ionic liquid through reactions with strong acids followed by a second reaction with a metal halide if needed. N-derivatized lactamium based ionic liquids can be used in numerous applications and can have an economic benefit.

One type of lactamium based ionic liquid has the general formula:

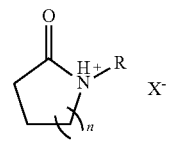
(I)

wherein R is an alkyl group having from 1 to 12 carbon atoms, an amine, an ether, or a silyl group, n is 1 to 8, and $X^-$ is an anion group of a Brønsted acid HX or a halometallate, with the proviso that when n is 3, $X^-$ is p-toluenesulfonate, and R is the alkyl group, the alkyl group has from 1 to 5 carbon atoms.

Another way to represent this compound is:

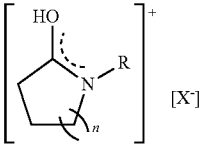

wherein R is an alkyl group having from 1 to 12 carbon atoms, an amine, an ether, or a silyl group, n is 1 to 8, and $X^-$ is an anion group of a Brønsted acid HX or a halometallate, with the proviso that when n is 3, $X^-$ is p-toluenesulfonate, and R is the alkyl group, the alkyl group has from 1 to 5 carbon atoms.

Formula (I) is intended to cover both representations.

Another type of lactamium based ionic liquid has the general formula:

(II)

wherein the ring has at least one C═C double bond, R is an alkyl group having from 1 to 12 carbon atoms, an amine, an ether, or a silyl group, n is 1 to 8, and $X^-$ is an anion group of a Brønsted acid HX or a halometallate.

The ring has at least one double bond. Larger rings may have more than one C═C double bond. The C═C double bond(s) can be between any two adjacent carbons capable of forming a double bond.

Another way to represent this compound is

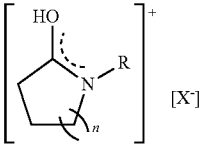

wherein the ring has at least one C═C double bond, R is an alkyl group having from 1 to 12 carbon atoms, an amine, an ether, or a silyl group, n is 1 to 8, and X⁻ is an anion group of a Brønsted acid HX or a halometallate.

Formula (II) is intended to cover both representations.

Examples of Formula (II) ionic liquids include, but are not limited to, 1,5-dihydro-1-methyl-2H-pyrrol-2-one based ionic liquids, and 1,3-dihydro-1-methyl-2H-pyrrol-2-one based ionic liquids.

Another type of lactamium based ionic liquid has the general formula:

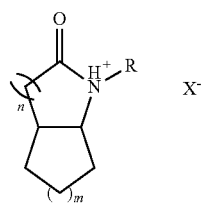

(III)

wherein R is an alkyl group having from 1 to 12 carbon atoms, an amine, an ether, or a silyl group, n is 1 to 8, m is 1 to 8, X⁻ is an anion group of a Brønsted acid HX or a halometallate, and the rings can be saturated or unsaturated.

The heterocyclic ring (ring with n) can be saturated or unsaturated. The hydrocarbon ring (ring with m) can be saturated, unsaturated, or aromatic. If the ring is unsaturated, the C=C double bond can be between any two adjacent carbons capable of forming a double bond. There can be one or more C=C double bonds in either ring or in both rings.

Another way to represent this compound is

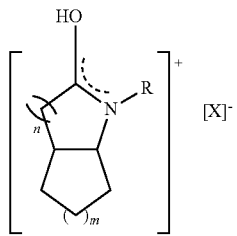

wherein R is an alkyl group having from 1 to 12 carbon atoms, an amine, an ether, or a silyl group, n is 1 to 8, m is 1 to 8, X⁻ is an anion group of a Brønsted acid HX or a halometallate, and the rings can be saturated or unsaturated.

The heterocyclic ring (ring with n) can be saturated or unsaturated. The hydrocarbon ring (ring with m) can be saturated, unsaturated, or aromatic. If the ring is unsaturated, the C=C double bond can be between any two adjacent carbons capable of forming a double bond. There can be one or more C=C double bonds in either ring or in both rings.

Formula (III) is intended to cover both representations.

Examples of Formula (III) ionic liquids include, but are not limited to, octahydro-1-methyl-2H-indol-2-one based ionic liquids, and 1,3-dihydro-1-methyl-2H-indol-2-one based ionic liquids.

Suitable X⁻ groups include, but are not limited to, carboxylates, nitrates, phosphates, phosphinates, phosphonates, imides, cyanates, borates, sulfates (including bisulfates), sulfonates (including fluoroalkanesulfonates), acetates, halides, halometallates, and combinations thereof. Examples of X⁻ groups include, but are not limited to, tetrafluoroborate, triflate, trifluoroacetate, chloroacetate, nitrate, hydrogen sulfate, hydrogen phosphate, dicyanoimide, methylsulfonate, and combinations thereof. Suitable halides include, but are not limited to, bromide, chloride, and iodide. Halometallates are mixtures of halides, such as bromide, chloride, and iodide, and metals. Suitable metals include, but are not limited to, Sn, Al, Zn, Mn, Fe, Ga, Cu, Ni, and Co. In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3$, $Cu_3Cl_4^-$, $ZnCl_3^-$, $FeCl_3^-$, $FeCl_4^-$, $Fe_3Cl_7$, $PF_6^-$, and $BF_4^-$.

In some embodiments, when making a halometallate, the lactam compound is reacted with a Brønsted acid HX, such as HCl, where X is a halide to form a lactamium halide. The lactamium halide is then reacted with a metal halide to form the lactamium halometallate.

As is understood by those of skill in the art, the particular Brønsted acid used will depend on the anion desired. Suitable Brønsted acids include for example, sulfuric acid, p-toluenesulfonic acid, hydrochloric acid, hydrobromic acid, nitric acid, phosphoric acid, tetrafluoroboric acid, triflic acid, trifluoroacetic acid, chloroacetic acid, and methanesulfonic acid.

A lactamium based ionic liquid can be made by reacting a lactam compound having a general formula

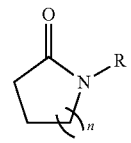

(IV)

wherein R is an alkyl group having from 1 to 12 carbon atoms, an amine, an ether, or a silyl group, n is 1 to 8;

with a Brønsted acid HX; or a Brønsted acid HX, where X is a halide, and a metal halide; with the proviso that when n is 3, the reaction product is p-toluenesulfonate, and R is the alkyl group, the alkyl group has from 1 to 5 carbon atoms.

Another lactamium based ionic liquid can be made by reacting a lactam compound having a general formula

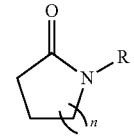

(V)

wherein the ring has at least one C=C double bond, R is an alkyl group having from 1 to 12 carbon atoms, an amine, an ether, or a silyl group, and n is 1 to 8, with a Brønsted acid HX; or a Brønsted acid HX, where X is a halide, and a metal halide.

Another lactamium based ionic liquid can be made by reacting a lactam compound having a general formula

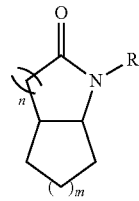

(VI)

wherein R is an alkyl group having from 1 to 12 carbon atoms, an amine, an ether, or a silyl group, n is 1 to 8, and m is 1 to 8, and the rings can be saturated or unsaturated;

with a Brønsted acid HX; or a Brønsted acid HX, where X is a halide, and a metal halide.

The heterocyclic ring (ring with n) can be saturated or unsaturated. The hydrocarbon ring (ring with m) can be saturated, unsaturated, or aromatic. If the ring is unsaturated, the C=C double bond can be between any two adjacent carbons capable of forming a double bond. There can be one or more C=C double bonds in either ring or in both rings.

The reaction can take place at temperatures in the range of about −36° C. to the decomposition temperature of the ionic liquid, or about −20° C. to less than the decomposition temperature of the ionic liquid, or about 0° C. to about 200° C., or about 0° C. to about 150° C., or about 0° C. to about 120° C., or about 20° C. to about 80° C.

The reaction typically takes place at atmospheric pressure, although higher or lower pressures could be used if desired.

When making halometallate compounds, the reaction should take place in an inert atmosphere.

The reaction typically takes about 1 min to multiple days, depending on the ionic liquid. Those made with the Brønsted acid typically take minutes to hours, while the halometallates typically take minutes to one or more days.

The reaction may be practiced in laboratory scale experiments through full scale commercial operations. The process may be operated in batch, continuous, or semi-continuous mode.

Typically, the ratio of the Brønsted acid to the lactam compound is about 1:1 to about 3:1. In some embodiments prior to making a halometallate, a lactamium halide is formed using a Brønsted acid to lactam compound ratio of about 1:1.

In some embodiments, the reaction can take place in the absence of a solvent. In other embodiments, it can take place in the presence of a solvent. Suitable solvents for non-halometallate ionic liquids include, but are not limited to, water, toluene, dichloromethane, liquid carboxylic acids, such as acetic acid or propanoic acid, alcohols, such as methanol and ethanol, and combinations thereof. When water is used as the solvent, an additional product may form. The products can be separated using known separation techniques. Non-protic solvents, such as dichloromethane, are suitable for use with halometallates.

By the term "about," we mean within 10% of the value, or within 5%, or within 1%.

EXAMPLES

Example 1

Preparation of N-Methylcaprolactamium Hydrogensulfate

In a 100 mL round bottom flask, sulfuric acid (0.77 g, 7.9 mmol) was added to a stirring solution of N-methylcaprolactam (1.00 g, 7.9 mmol) in toluene (5 mL). After stirring for four hours at room temperature, volatiles were removed producing a light orange liquid. Yield: 1.75 g, 98.4%. $^1$H NMR (500 MHz, CDCl3): 1.70 (m, 6H), 2.63 (t, 2H), 3.03 (s, 3H), 3.41 (t, 2H), 7.79 (br).

Example 2

Preparation of N-Methylcaprolactamium p-Toluenesulfonate

In a 100 mL round bottom flask, p-toluenesulfonic acid monohydrate (1.35 g, 7.9 mmol) was added to a stirring solution of N-methylcaprolactam (1.00 g, 7.9 mmol) in water (5 mL). After stirring for four hours at room temperature, volatiles were removed producing an orange liquid. Yield: 2.48 g. $^1$H NMR (500 MHz, CDCl3): 1.70 (m, 6H), 2.36 (s, 3H), 2.77 (t, 2H), 3.03 (s, 3H), 3.48 (t, 2H), 7.20 (d, 2H), 7.77 (d, 2H), 8.05 (s, 2H).

Example 3

Preparation of N-Methylcaprolactamium Chloride

In a 100 mL round bottom flask, a solution of hydrochloric acid (5.28 g, 0.047 mol) was added to caprolactam (6.02 g, 0.047 mmol). After stirring for 0.75 h, volatiles were removed. If two compounds result due to the presence of water, distillation may be used to separate the mixture. $^1$H NMR (500 MHz, $d_6$-DMSO): 1.46-1.63 (m, 6H), 2.40 (t, 2H), 2.81 (s, 3H), 3.33 (t, 2H). $^{13}$C NMR (125 MHz, $d_6$-DMSO): 23.23, 27.40, 29.43, 35.65, 36.1, 50.88, 175.79.

Example 4

Preparation of N-Methylcaprolactamium Nitrate

In a 100 mL round bottom flask, nitric acid (0.51 g, 8.1 mmol) was added to a stirring solution of N-methylcaprolactam (1.02 g, 8.0 mmol) in water (5 mL). After stirring for four hours at room temperature, volatiles were removed producing a yellow orange liquid. Yield: 1.44 g, 94.6%. $^1$H NMR (500 MHz, CDCl3): 1.70 (m, 6H), 2.65 (t, 2H), 3.09 (s, 3H), 3.48 (t 2H), 11.51 (br s, 2H).

Example 5

Preparation of N-Methylcaprolactamium Chloroaluminate

In a round bottom flask in a nitrogen atmosphere, AlCl$_3$ (8.10 g, 0.061 mol) was slowly added to N-methylcaprolactamium chloride (5.02 g, 0.031 mol). After stirring for 1.5 h, the reaction mixture was allowed to settle. The liquid was decanted from any remaining solids. Yield: 12.5 (94%). $^1$H NMR (500 MHz, CDCl3): 1.84-1.81 (m, 6H), 2.98 (t, 2H), 3.32 (s, 3H), 3.75 (t, 2H). $^{13}$C NMR (125 MHz, CDCl3): 21.37, 24.95, 28.88, 35.59, 39.76, 54.67, 178.05.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:
1. A lactamium based ionic liquid consisting of:
a reaction product of a lactam compound having a formula
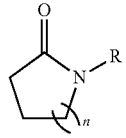
(IV)
wherein R is an alkyl group having from 1 to 12 carbon atoms, n is 3; and a Brønsted acid HX where X is a halide, and a metal halide where the reaction product is a halometallate.
* * * * *